US00PP20526P3

(12) United States Plant Patent
Toyama

(10) Patent No.: US PP20,526 P3
(45) Date of Patent: Dec. 8, 2009

(54) CHERRY TREE NAMED 'PC8007-2'

(50) Latin Name: *Prunus avium*
Varietal Denomination: PC8007-2

(75) Inventor: Thomas K. Toyama, Eugene, OR (US)

(73) Assignee: Washington State University Research Foundation, Pullman, WA (US)

( * ) Notice: Subject to any disclaimer, the term of this patent is extended or adjusted under 35 U.S.C. 154(b) by 161 days.

(21) Appl. No.: 11/895,279

(22) Filed: Aug. 22, 2007

(65) Prior Publication Data

US 2008/0184432 P1 Jul. 31, 2008

Related U.S. Application Data

(60) Provisional application No. 60/839,924, filed on Aug. 23, 2006.

(51) Int. Cl.
*A01H 5/00* (2006.01)

(52) U.S. Cl. ..... Plt./181

(58) Field of Classification Search ..... Plt./181
See application file for complete search history.

(56) References Cited

OTHER PUBLICATIONS

2005 Fruit characteristics of sweet cherry cultivars and selections under evaluation in the Dalles ath the Cemetery Block N=25, [online], [retrieved Jun. 24, 2008]. Retrieved from the Internet: <http://extension.oregonstate.edu/wasco/horticulture/Research%20Reports/documents/CemeteryBlockCompleteVarietyResults2005edit0914.pdf> 1page.*

Upov International Union for the Protection of New Varieties of Plants, Explanatory notes on variety denominations under the Upov convention. Oct. 19, 2006, page 4.*

* cited by examiner

*Primary Examiner*—David H Kruse
*Assistant Examiner*—June Hwu
(74) *Attorney, Agent, or Firm*—Michelle Bos

(57) ABSTRACT

A new cultivar of sweet cherry tree named 'PC8007-2' is disclosed. The new cultivar is notable for its firm, flavorful fruit.

1 Drawing Sheet

Latin name of the genus and species of the plant claimed: *Prunus avium.*

Variety denomination: 'PC8007-2'.

BRIEF DESCRIPTION OF THE PHOTOGRAPHS

The photograph shows the fruit of the new cultivar.

DETAILED BOTANICAL DESCRIPTION OF THE VARIETY

The present invention relates to a new variety of sweet cherry tree named 'PC8007-2.' 'PC8007-2' was developed at the Washington State University Irrigated Agriculture Research and Extension Center (I.A.R.E.C.) at Prosser, Wash. It was selected from among several seedlings that resulted from a controlled cross made in 1980 between 'PC7144-7' (female parent, not patented) and 'PC7144-3' (male parent, not patented), and has continued to be tested as 'PC8007-2.'

Asexual reproduction of this new and distinct cultivar at test facilities near Prosser shows that its desirable characteristics come true to form and are established and transmitted through succeeding propagations by grafting.

The following is a detailed botanical description of 'PC8007-2,' based on observations made during the 2007 growing season in Prosser, Wash., of 25 year old trees grown on Mazzard rootstock. It should be understood that the botanical and analytical characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree: Semi-vigorous, productive; Height 5 m, spread 8.8 m; Trunk — diameter 57 cm at 15 cm above soil, bark rough, greyed-green 197A, trunk lenticel color greyed-orange 164B, trunk lenticels 5.5 mm, numerous; Branch — diameter 20.8 cm, length 4.6 m, crotch angle 48°, texture medium to rough, first year wood greyed-red 178B and greyed-brown 199D, second year wood greyed-red 182C and greyed-brown 199B, branch lenticels 9.6 mm, numerous, greyed-brown 199B.

Leaves: Size — length 13 mm, width 6 mm; Shape — elliptic, acute tip, rounded base, serrated margin; Color — upper surface green 141B, lower surface green 143A, midvein upper surface yellow-green 146C, midvein lower surface yellow-green 146C; Petiole — length 3.8 mm, diameter 1.6 mm; upper surface greyed-orange 166A, lower surface greyed-orange 166B; Glands — Quantity 2, reniform, length 2 mm, width 1 mm, color greyed-purple 185B.

Bloom time: 2 days later than 'Bing'

Fruit: Size — wide plane diameter 29.0 mm, narrow plane diameter 24.8 mm, height 26.5 mm, weight 12.1 g; Shape — symmetrical; Suture — present, depth 0.4 mm; Stem — length 43.1 mm, diameter 1.2 mm, yellow-green 145A; Cavity — depth 1.5 mm, diameter 11.9 mm; Skin — smooth, thickness 0.5 mm, low tenacity, moderate tendency to crack, red-purple 59A; Flesh — red-purple 59A, smooth, medium juiciness, excellent eating quality; Stone — length 12.4 mm, width 7.5 mm, broad elliptic, tenacious, greyed-orange 164C.

Harvest: First picking June 18, last picking June 23, maturity date June 20 (2007 growing season, Prosser, Wash.).

I claim:

1. A new and distinct cherry tree, substantially as shown and described herein.

* * * * *

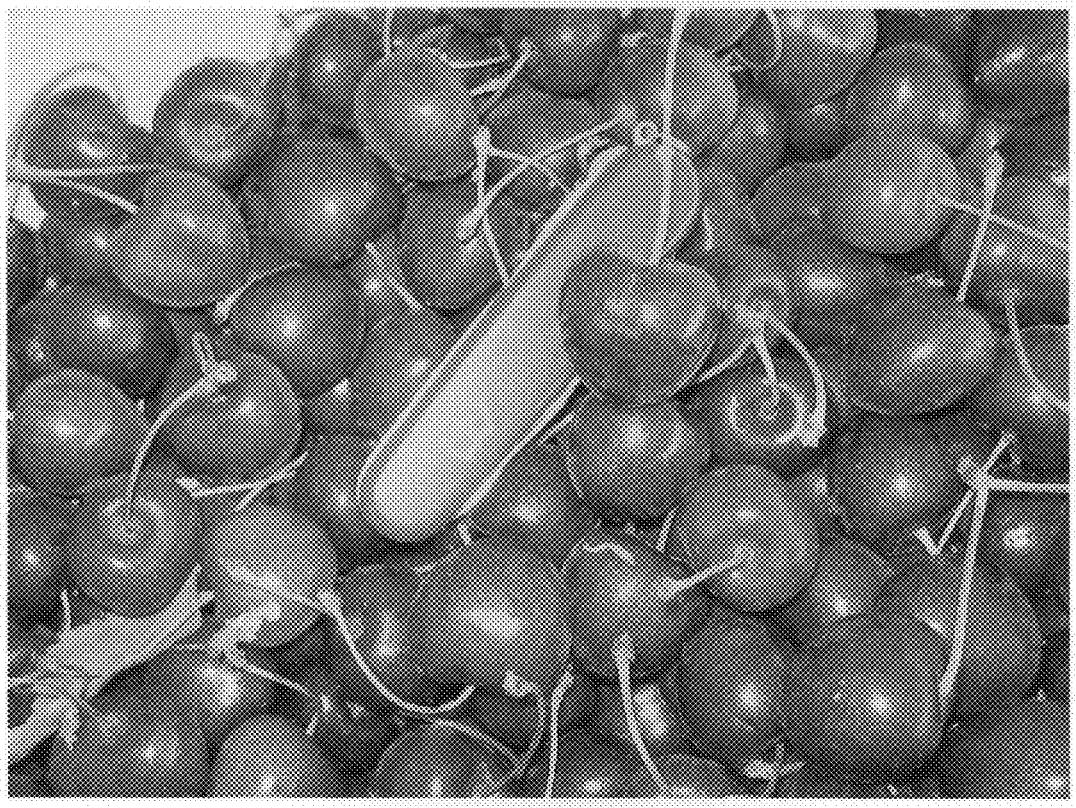

UNITED STATES PATENT AND TRADEMARK OFFICE

CERTIFICATE OF CORRECTION

PATENT NO. : PP 20,526 P3
APPLICATION NO. : 11/895279
DATED : December 8, 2009
INVENTOR(S) : Thomas K. Toyama It is certified that error appears in the above-identified patent and that said Letters Patent is hereby corrected as shown below:

In Column 1:

At line 16, "not patented" should read --U.S. Plant Patent No. 8051--;

Before the paragraph beginning at line 19, the following text and table should be inserted:

--'PC8007-2' is a 'Bing' type cherry, and is distinguished from 'Bing' and from its parents by several characteristics, as set forth in the table below.

| | 'PC7144-7' | 'PC7144-3' | 'PC8007-2' |
|---|---|---|---|
| Fertility | Self-fertile | Self-fertile | Pollenizer required |
| Maturity Date | 4-5 days before 'Bing' | 8-11 days before 'Bing' | 4-7 days before 'Bing' |
| Fruit Size | Large | Medium to large | Large |
| Stem Length | Medium to long | Medium to long | Long-- |

After line 32, the following sentence should be inserted: --Color descriptions are made with reference to the Royal Horticultural Society Colour Chart.--.

In Column 2:

At line 9, after "199B" insert --; Heat/cold resistance – hardy in area where tested--;

At line 10, "13 mm" should read --13 cm-- and "6 mm" should read --6 cm--;

At line 17, delete "Bloom time: 2 days later than 'Bing'" and insert the following new paragraph:

--Flowers: Buds – 5 to 7 per spur (avg. 6), conical, length 9.2 mm, diameter 4.9 mm; color brown 200C; Blossoms – 2 to 3 per bud, diameter 4.2 cm, depth 7.6 mm; Petals – 5 per flower, not touching, elliptic to broad elliptic, length 17.6 mm, width 12.0 mm, apex retuse, margin smooth, white upper and lower surface; Pistils – carpel length 15.0 mm, style length 10.0 mm, style diameter 0.5 mm, style color yellow-green 151A; Stigma – Elliptic, diameter 1.0 mm, color yellow-green N144A; Ovary – Diameter 2.4 mm, length 3.2 mm, color yellow-green 143A; Stamens – 40 per flower, filament length 8.1 mm, color 155C, anther heart shaped, width 1 mm, color 163B, pollen present, color yellow; Pedicel – length 23.7, diameter 1.1 mm; color green 138A; Sepals – quantity 5, upper color green 138B with highlights of orange-red N34A, lower color green 138B, length 6.4 mm, width 4.8 mm, shape elliptical, apex obtuse, base truncate, margin smooth, texture smooth; Full bloom – 2 days later than 'Bing' (April 24, 2009 in Prosser, Washington).--;

In Column 2:

At line 20, after "Shape -" insert --cordate,-- and after "symmetrical" insert --, apex pointed--; and
At line 24, after "59A;" insert --Firmness - firm, 280g;--.

Signed and Sealed this

Sixth Day of April, 2010

David J. Kappos

David J. Kappos
*Director of the United States Patent and Trademark Office*